(12) United States Patent
Baert et al.

(10) Patent No.: US 10,765,674 B2
(45) Date of Patent: Sep. 8, 2020

(54) PREVENTION OF HIV-INFECTION

(71) Applicant: Janssen Sciences Ireland Unlimited Company, Co Cork (IE)

(72) Inventors: Lieven Elvire Colette Baert, Bruges (BE); Paulus Joannes Lewi, Turnhout (BE); Jan Heeres, Vosselaar (BE)

(73) Assignee: Janssen Sciences Ireland Unlimited Company, Co Cork (IE)

( * ) Notice: Subject to any disclaimer, the term of this patent is extended or adjusted under 35 U.S.C. 154(b) by 470 days.

(21) Appl. No.: 15/180,391

(22) Filed: Jun. 13, 2016

(65) Prior Publication Data

US 2016/0296519 A1  Oct. 13, 2016

Related U.S. Application Data

(63) Continuation of application No. 15/017,168, filed on Feb. 5, 2016, now abandoned, which is a continuation of application No. 12/961,305, filed on Dec. 6, 2010, now abandoned, which is a continuation of application No. 11/910,034, filed as application No. PCT/EP2006/061303 on Apr. 4, 2006, now abandoned.

(30) Foreign Application Priority Data

Apr. 4, 2005 (EP) .................................. 05102616

(51) Int. Cl.
*A61K 31/505* (2006.01)
*A61K 47/10* (2017.01)
*A61K 47/16* (2006.01)
*A61K 9/00* (2006.01)

(52) U.S. Cl.
CPC .......... *A61K 31/505* (2013.01); *A61K 9/0019* (2013.01); *A61K 47/10* (2013.01); *A61K 47/16* (2013.01)

(58) Field of Classification Search
CPC .... A61K 31/505; A61K 9/0019; A61K 47/10; A61K 47/16
USPC ....................................................... 514/275
See application file for complete search history.

(56) References Cited

U.S. PATENT DOCUMENTS

2004/0115268 A1* 6/2004 Ashton ................ A61K 9/0004
424/473

FOREIGN PATENT DOCUMENTS

| WO | WO 2001/010456 A2 | 2/2001 |
| WO | WO 2001/074329 A2 | 10/2001 |
| WO | WO 2003/016306 A1 | 2/2003 |
| WO | WO 2004/043433 A2 | 5/2004 |
| WO | WO 2004/046309 A2 | 6/2004 |
| WO | WO 2004/069812 A1 | 8/2004 |
| WO | WO 2004/073703 A1 | 9/2004 |
| WO | WO 2005/021001 A1 | 3/2005 |

OTHER PUBLICATIONS

Farquhar, Cary, et al., "Salivary Secretary of Leukocyte Protease Inhibitor is Associated With Reduced Transmission of Human Immunodeficiency Virus Type 1 Through Breast Milk", The Journal of Infectious Diseases, 2002, vol. 186, pp. 1173-1176, Infectious Diseases Society of America.
Gulick R.M. : 'New Antiretroviral Drugs', Clinical Microbiology and Infection, vol. 9, 2003, pp. 186-193.
Janssen et al., "In Search of a Novel Anti-HIV Drug: Multidisciplinary Coordination in the Discovery of 4-[[4-[[4-[(1E)-2-Cyanoethenyl]-2,6-dimethylphenyl]amino]-2-pyrimidinyl]amino]benzonitrile (R278474, Rilpivirine)", J. Med. Chem., vol. 48, pp. 2901-1909 (2005).
McNeely, Tessie B., et al., "Secretory Leukocyte Protease Inhibitor: A Human Saliva Protein Exhibiting Anti-Human Immunodeficiency Virus 1 Activity in Vitro", The Journal of Clinical Investigation, Inc., 1995, vol. 96, pp. 456-464.
Susman, Edward, "Retroviruses and Opportunistic Infections—12$^{th}$ Conference", Idrugs, vol. 8, No. 4, pp. 299-302 (2005) (XP008051947).
Wahl, Sharon M., "Anatomic Dissociation between HIV-1 and Its Endogenous Inhibitor in Mucosal Tissues", American Journal of Pathology, 1997, vol. 150, No. 4, pp. 1275-1284, American Society for Investigative Pathology.
Patent Abstracts of Japan, vol. 1995, No. 2 & JP 06 316524 A Abstract.
International Search Report and Written Opinion dated Mar. 27, 2007, for Corresponding International Application PCT/EP2006/061303.
Okwundu et al., "Antiretroviral pre-exposure prophylaxis (PrEP) for preventing HIV in high-risk individuals", the Cochrane Library, Issue 4, p. 1-23, 2009.
Romano et al., "Pharmacokinetics and Pharmacodynamics in HIV Prevention; Current Status and Further Directions: A Summary of the DAIDS and BMGF Sponsored Think Tank on Pharmacokinetics (PK)/Pharmacodynamics (PD) in HIV Prevention", AIDS Research and Human Retroviruses, 29(11), p. 1418-1427, 2013.
Jackson et al., "Rilpavirine-LA Formulation: Pharmacokinetics in Plasma, Genital Tract in HIV Females and Rectum in Males", Paper #35, CROI 2012 Seattle, Washington State Convention Center, Mar. 5-8, 2012, 2pgs.
José Vila Jato: Pharmaceutical Technology, vol. II, Chapter 3: Injectables, pp. 157-249 (Nov. 30, 1999).

* cited by examiner

*Primary Examiner* — Yevgeny Valenrod

(57) ABSTRACT

This invention relates to the use of a parenteral formulation comprising the NNRTI TMC278 for the long term prevention of HIV infection in a subject at risk of being infected by HIV, which comprises the intermittent administration of the said formulation at long time intervals.

24 Claims, No Drawings

PREVENTION OF HIV-INFECTION

CROSS-REFERENCE TO RELATED APPLICATIONS

This application is a continuation of U.S. patent application Ser. No. 15/017,168, filed on Feb. 5, 2016, which is a continuation of U.S. patent application Ser. No. 12/961,305, filed on Dec. 6, 2010, which is a continuation of U.S. patent application Ser. No. 11/910,034, filed on Sep. 28, 2007, now abandoned, which is a national phase entry of International Application No. PCT/EP2006/061303, filed on Apr. 4, 2006, which claims priority to EP Patent Application No. 05102616.9, filed on Apr. 4, 2005, each of which is incorporated herein in its entirety.

FIELD OF THE INVENTION

This invention relates to the use of a parenteral formulation comprising the NNRTI TMC278 for the long term prevention of HIV infection in a subject at risk of being infected by HIV, which comprises the intermittent administration of the said formulation at long time intervals.

BACKGROUND OF THE INVENTION

The treatment of Human Immunodeficiency Virus (HIV) infection, which is causative to the acquired immunodeficiency syndrome (AIDS), remains a major medical challenge. HIV is able to evade immunological pressure, to adapt to a variety of cell types and growth conditions and to develop resistance against currently available drug therapies. The latter include nucleoside reverse transcriptase inhibitors (NRTIs), non-nucleoside reverse transcriptase inhibitors (NNRTIs), nucleotide reverse transcriptase inhibitors (NtRTIs), HIV-protease inhibitors (PIs) and the more recent fusion inhibitors.

Each of these drugs can only transiently restrain viral replication if used alone.

Insufficient drug potency, non-compliance, restricted tissue penetration and drug-specific limitations within certain cell types are amongst the factors that account for the incomplete suppression of HIV. This led to the introduction of combination therapy of several anti-HIV agents having a different activity profile. Significant progress was made by the introduction of "HAART" (Highly Active Anti-Retroviral Therapy), which has resulted in a significant reduction of morbidity and mortality in HIV patient populations treated therewith. Current guidelines for antiretroviral therapy recommend such triple combination therapy regimen even for initial treatment. However, none of the currently available drug therapies is capable of completely eradicating in HIV and long-term treatment usually results in suppressing virus replication to a level where it no longer can cause the outbreak of the symptoms associated with AIDS.

Currently used anti-HIV drugs require frequent administration of relatively high doses. The number and/or volume of dosage forms that need to be administered is commonly referred to as the "pill burden". A high pill burden is undesirable for many reasons, such as the patient having to spend more time taking each dose and the patient having to store and/or transport a large number or volume of pills. A high pill burden also increases the risk that a patient will not take his or her entire dose, thereby failing to comply with the prescribed dosage regimen. As well as reducing the effectiveness of the treatment for that patient, this may also lead to the disease-causing organism or virus becoming resistant to the pharmaceutical agent.

Individuals infected by HIV virus often are unaware of the fact that they carry the virus and therefore constitute a continuous risk of transferring the infection to others. Even in developed countries this is still the case but in particular is a threat in many of the less-developed countries, where people have no or limited access to medical care, including to HIV diagnostic tools. Therefore, prevention of HIV transmission is a crucial component in the battle against the spread of HIV. Prevention currently focuses on avoiding sexual transmission, in particular by promoting the use of condoms in populations at risk of being infected, the careful monitoring of blood samples for the presence of HIV and the avoiding of contact with blood of potentially infected subjects.

Despite these measures there is always an imminent risk for certain population groups to become infected with HIV. This in particular is the case for those providing medical care to infected patients such as physicians, nurses and dentists. Other population groups at risk for example are breast-fed infants where the mother is infected, especially in developing countries where alternatives for breast-feeding are less obvious.

Hence there is a need for further means that provide prevention against transmission of HIV. There is a particular need for effective prevention means that are easy to apply. Providing such prevention means is an object of the present invention.

It now has been found that intermittent administration of parenteral formulations of the NNRTI TMC278 at time intervals of one week or longer result in plasma levels that are sufficient to provide prevention against transmission of HIV. A reduced number of administrations are needed which is advantageous in terms of pill burden and drug compliance of the individual at risk of being infected.

TMC278 is an NNRTI that currently is in clinical development. This compound is a highly potent drug not only showing pronounced activity against wild type HIV, but also against many of its mutated variants. The compound TMC278, its pharmacological activity as well as a number of procedures for its preparation have been described in WO-03/16306. Various conventional pharmaceutical dosage forms, including tablets, capsules, drops, suppositories, oral solutions and injectable solutions are exemplified therein.

SUMMARY OF THE INVENTION

In one aspect, the present invention relates to the use of a parenteral formulation comprising an effective amount of TMC278 or a pharmaceutically acceptable acid-addition salt thereof, and a carrier, for the manufacture of a medicament for the long term prevention of HIV infection in an individual at risk of being infected by HIV, wherein the formulation is administered intermittently at a time interval of at least one week.

In another aspect the invention relates to a method for the long term prevention of HIV infection in an individual at risk of being infected by HIV, said method comprising administering an effective amount of TMC278 or a pharmaceutically acceptable acid-addition salt thereof, and a carrier, to said individual, wherein the formulation is administered intermittently at a time interval of at least one week.

DETAILED DESCRIPTION OF THE INVENTION

The compound used in the invention is the compound TMC278 (also referred to as R278474) or 4-[[4-[[4-(2- cyanoethenyl)-2,6-dimethylphenyl]amino]-2-pyrimidinyl]-amino]benzonitrile which is a known NNRTI currently in clinical development as HIV inhibitor. This compound, its properties and its preparation have been described in WO-03/016306.

TMC278 can be used in base form or as a suitable pharmaceutically acceptable salt form, such as an acid addition salt form. The pharmaceutically acceptable addition salts are meant to comprise the therapeutically active non-toxic salt forms. The acid addition salt forms can be obtained by treating the base form with appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Preferred for use in the present invention is the base form of TMC278.

The terms salt or salt form also comprises the hydrates and the solvent addition forms which the compound TMC278 is able to form. Examples of such forms are e.g. hydrates, alcoholates and the like.

TMC278 occurs in stereoisomeric forms, more in particular as E- and Z-isomeric forms. Both isomers may be used in the present invention. Whenever reference is made herein to TMC278, the E- or the Z-form as well as any mixture of both forms are meant to be included. A preferred form of TMC278 for use in the invention is the E-isomer, i.e. (E)-4-[[4-[[4-(2-cyanoethenyl)-2,6-dimethylphenyl]-amino]-2-pyrimidinyl]-amino]-benzonitrile, which may be referred to as E-TMC278. The Z-isomer of TMC278, i.e. (Z)-4-[[4-[[4-(2-cyanoethenyl)-2,6-dimethylphenyl]-amino]-2-pyrimidinyl]-amino]-benzonitrile, which may be referred to as Z-TMC278, can also be used.

Whenever reference is made herein to the E-form of TMC278 (i.e. E-TMC278), the pure E-isomer or any isomeric mixture of the E- and the Z-forms wherein the E-form is predominantly present is meant to be comprised, i.e. an isomeric mixture containing more than 50% or in particular more than 80% of the E-form, or even more than 90% of the E-form. Of particular interest is the E-form substantially free of the Z-form. Substantially free in this context refers to E-Z-mixtures with no or almost no Z-form, e.g. isomeric mixtures containing as much as 90%, in particular 95% or even 98% or 99% of the E-form. Equally, whenever reference is made herein to the Z-form of TMC278 (i.e. Z-TMC278), the pure Z-isomer or any isomeric mixture of the Z- and the E-forms wherein the Z-form is predominantly present is meant to be comprised, i.e. an isomeric mixture containing more than 50% or in particular more than 80% of the Z-form, or even more than 90% of the Z-form. The Z-form substantially free of the E-form can also be used. Substantially free in this context refers to E-Z-mixtures with no or almost no E-form, e.g. isomeric mixtures containing as much as 90%, in particular 95% or even 98% or 99% of the Z-form.

Also meant to be included for use in this invention are salts of the stereoisomeric forms of TMC278, in particular the salts mentioned above, e.g. Z-TMC278 hydrochloride and E-TMC278 hydrochloride.

Whenever used herein, the term "TMC278" refers to as well the base form as any pharmaceutically acceptable acid-addition salt thereof, and also to the stereoisomeric forms of TMC278 as well as any pharmaceutically acceptable acid-addition salt of said stereoisomeric forms. In particular, the term "TMC278" refers to the E-isomer of TMC278 as well as its pharmaceutically acceptable acid-addition salts.

The parenteral formulations of TMC278 are administered intermittently at a time interval of at least one week, meaning that the parenteral formulation is administered without any interjacent additional administrations of TMC278. Or with other words, TMC278 is administered at particular points in time separated from one another by a time period of at least one week during which no TMC278 is administered. Hence the administration schedule is simple, requiring few administrations, i.e. involves limited "pill burden". All this contributes beneficially to the patient's compliance to the prescribed dosing regimen.

The parenteral formulations of TMC278 are administered at time intervals of at least one week, but may also be administered at longer time intervals such as several weeks, e.g. 2, 3, 4, 5 or 6 weeks, or at time intervals of one month, or of several months, e.g. 2, 3, 4, 5 or 6 months or even longer, e.g. 7, 8, 9 or 12 months. In one embodiment, the parenteral formulation is administered at a time interval of one, two or three months. These longer periods between each administration of the parenteral formulation consist in an even further improvement of "pill burden" and compliance. To further improve compliance, the patient can be instructed to take his or her medication at a certain day of the week, where the formulation is administered on a weekly schedule, or at a certain day of the month in case of a monthly schedule.

The uses and methods in accordance with this invention are for the long term prevention of HIV infection, or with other words for the prevention during a prolonged period of time.

With "long term" for example as used in relation to "long term prevention of HIV infection" or "prolonged period of time", there is meant a term of several days, e.g. 7, 10 or 12 days, or several weeks, e.g. 2, 3 or 4 weeks, or one month, or several months, e.g. 2, 3, 4, 5 or six months or even longer, e.g. 7, 8, 9 or 12 months. In preferred embodiments the methods and uses in accordance with the present invention are for the prevention of HIV infection during one month, or several months, as mentioned above.

The term "prevention of HIV infection" relates to the prevention or avoidance of an individual becoming infected with HIV. The source of infection is usually another individual who is infected with HIV and prevention of HIV infection in this instance relates to the prevention of the transmission of the virus from the infected individual to an uninfected person, or the prevention of the virus from entering the body from an uninfected person. Transmission of the HIV virus can be by any known cause of HIV transfer such as by sexual transmission or by contact with blood from an infected individual, e.g. medical staff providing care to infected individuals. Transfer of HIV can also occur by contact with HIV infected blood, e.g. when handling blood samples or with blood transfusion. It can also be by contact with infected cells, e.g. when carrying out laboratory experiments with HIV infected cells.

With "efficacious blood plasma levels" is meant those blood plasma levels of the HIV inhibitor TMC278 that provide effective prevention of HIV infection.

Preferably the parenteral formulation is administered in a single administration, for example by one injection after a time interval of at least one week, e.g by one injection every week or by one injection every month.

The concentration (or "C") of TMC278 in the blood plasma of a subject treated therewith is generally expressed as mass per unit volume, typically nanograms per milliliter (ng/ml). For convenience, this concentration may be referred to herein as "blood plasma drug concentration" or "blood plasma concentration".

The dose of TMC278 administered, which is the amount of TMC278 in the parenteral formulation for use in the invention, is selected such that the blood plasma concentration of TMC278 is kept during a prolonged period of time above a minimum blood plasma level. The term "minimum blood plasma level" (or $C_{min}$) in this context refers to the lowest efficacious blood plasma level, the latter being that blood plasma level of TMC278 that provides effective prevention of HIV infection. In the case of transmission of HIV from an individual infected by HIV to an individual not infected by HIV, this is the lowest blood plasma level that is effective in inhibiting said transmission.

In particular, the blood plasma level of TMC278 is kept at a level above a minimum blood plasma level of about 4 ng/ml, more in particular about 5 ng/ml, or 8 ng/ml, further in particular about 10 ng/ml, still more in particular about 15 ng/ml, or in certain cases above a level of about 20 ng/ml or even 40 ng/ml. The blood plasma levels of TMC278 should preferably be kept above these mininum blood plasma levels because at lower levels the drug may no longer be effective thereby increasing the risk of transmission of HIV infection. Plasma levels of TMC278 may be kept at somewhat higher levels to have a safety margin and to avoid the development of mutated HIV.

An advantage of TMC278 is that it can be used up to relatively high blood plasma levels without any significant side effects. This means that the maximum plasma level is not so critical. The plasma concentrations of TMC278 may reach be relatively high levels, but as with any drug should not exceed a maximum plasma level (or $C_{max}$), which is the blood plasma level where TMC278 causes significant side effects. As used herein, the term "significant side effects" means that the side effects are present in a relevant patient population to an extend that the side effects affect the patients' normal functioning. The $C_{max}$ for TMC278 can be determined from the extrapolation of test data in cellular assays or from the evaluation of clinical testing and preferably should not exceed a value of about 500 ng/ml or even 1000 ng/ml.

Therefore, in most cases, the effective amount of TMC278 to be administered is selected such that the blood plasma concentrations are kept during a prolonged period of time at a level comprised between a maximum plasma level (or $C_{max}$ as specified above) and the minimum blood plasma level (or $C_{min}$ as specified above).

In certain instances it may be desirable to keep the plasma levels of TMC278 at relatively low levels, e.g. as close as possible to the minimum blood plasma levels specified herein. This will allow reducing the frequency of the administrations and/or the quantity of TMC278 administered with each administration. It will also allow avoiding undesirable side effects, which will contribute to the acceptance of the dosage forms in most of the targeted population groups who are healthy people at risk of being infected and therefore are less inclined to tolerate side effects.

Of particular interest are uses or methods as specified above and further specified in this description and claims wherein the maximum blood plasma level of TMC278 is about equal to the lowest blood plasma level that causes the RT inhibitor to act therapeutically.

In some embodiments the blood plasma level of TMC278 is kept between the minimum blood plasma level (or $C_{min}$ as specified above) and the lower maximum plasma level of TMC278 (or $C'_{max}$) which is defined as the level, that corresponds to the lowest blood plasma level where TMC278 acts therapeutically. The lowest level where TMC278 acts therapeutically is the lowest blood plasma level that is effective in inhibiting replication of HIV in individuals infected by HIV so that the viral load of HIV is relatively low, for example where the viral load (represented as the number of copies of viral RNA in a specified volume of serum) is below about 200 copies/ml, in particular below about 100 copies/ml, more in particular below 50 copies/ml, specifically below the detection limit of the virus.

In other embodiments, the blood plasma level of TMC278 is kept at a level below a lower maximum blood plasma level of about 10 ng/ml, more in particular about 15 ng/ml, further in particular about 20 ng/ml, still more in particular about 40 ng/ml. In a particular embodiment, the blood plasma level of TMC278 is kept below a level of about 13.5 ng/ml. In one embodiment, the plasma level of TMC 278 is kept in an interval of the lower maximum blood level specified above, and the minimum blood plasma levels mentioned in this paragraph. For example the blood plasma levels of TMC278 are kept below about 10 ng/ml and above a minimum level of about 4 ng/ml.

In other instances it may be desirable to keep the plasma levels of TMC278 at relatively higher levels, for example where there is a high risk of infection and more frequent and/or higher doses are not an issue. In these instances the minimum blood plasma level (or $C'_{min}$) may equal the lowest blood plasma level where TMC278 acts therapeutically As mentioned above, the blood plasma levels of TMC278 depend on the amount of active ingredient in each parenteral dosage administered. However it also depends on the frequency of the administrations (i.e. the time interval between each administration). Both parameters can be used to direct the blood plasma levels to the desired values. The dose will be higher where administrations are less frequent.

Although the plasma levels of TMC278 should remain below a maximum or above a minimum value, they may surpass the maximal value or drop below the minimal value during relatively short periods of time, which should be as short as possible. The maximum and minimum plasma levels therefore can be expressed as mean plasma levels during a certain period of time, e.g. for equal or more than 15 minutes.

In some instances there may be a small initial plasma concentration peak shortly after administration, after which the plasma levels achieve a "steady-state" as mentioned above.

The dose to be administered should be calculated on a basis of about 0.2 mg/day to about 50 mg/day, in particular 0.5 mg/day to about 50 mg/day, more in particular of about 1 mg/day to about 10 mg/day, or about 2 mg/day to about 5 mg/day, e.g. about 5 mg/day. This corresponds to a weekly dose of about 1.5 mg to about 350 mg, in particular of about 3.5 mg to about 350 mg, in particular of about 7 mg to about 70 mg, or about 14 mg to about 35 mg, e.g. about 35 mg, or to a monthly dose of from 6 mg to about 350 mg, in particular about 15 mg to about 1,500 mg, more in particular of about 30 mg to about 300 mg, or about 60 mg to about 150 mg, e.g. about 150 mg. Doses for other dosing regimens can readily be calculated by multiplying the daily dose with the number of days between each administration.

It has been found that, once administered, the blood plasma levels of TMC278 are more or less stable, i.e. they fluctuate within limited margins. The blood plasma levels have been found to approach a steady state mode during a prolonged period of time. By "steady state" is meant the condition in which the amount of drug present in the blood plasma of a subject stays at more or less the same level over a prolonged period of time. The plasma levels of TMC278 generally do not show any drops below the minimum plasma level at which the drug is effective. The term "stays at more or less the same level" does not exclude that there can be small fluctuations of the plasma concentrations within an acceptable range, e.g. within about 30% in particular, within about 20%, further in particular within about 10%.

The parenteral TMC278 formulations may be administered by intravenous injection or, which is preferred by subcutaneous or intramuscular administration.

The present invention is based on the use of parenteral formulations of the active ingredient TMC278 and therefore the nature of the carrier will have to be selected such as to suit parenteral administration. The carrier in most cases will comprise sterile water, at least in large part, though other ingredients, for example, to aid solubility, may be included. Injectable solutions, for example, may be prepared in which the carrier comprises saline solution, glucose solution or a mixture of saline and glucose solution.

To enhance solubility of the active compound additional ingredients may be added that have a solubility promoting effects such solubilizers and surfactants. Examples of solubilizers are cyclodextrins or cyclodextrin derivatives or polyethylene glycols (PEGs) such as PEG 400. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy $C_{1-6}$alkyl, particularly hydroxyethyl, hydroxy-propyl or hydroxybutyl; carboxy $C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD). Surfactants comprise polyethoxylated sorbitan ethers such as the Tween™ series of surfactants, e.g. Tween 20™.

In some instances, the parenteral formulations with TMC278 may be formulated with or in a suitable controlled release or sustained release carrier and are referred to as controlled or sustained release formulations. Such formulations may be selected to better control fluctuations in the blood plasma levels and/or to prolong the release of the active ingredient, e.g. where periods between each administration of a month or several months are desired.

As used herein "controlled release" refers to the constant release of active ingredients without peaks or drops in the release of the active ingredients during a certain period of time. "Sustained release" refers to the situation where the release of active ingredient is prolonged in some way in order to maintain effective blood plasma levels for an extended period of time. Sustained release dosage forms usually also show controlled release of the active ingredient during a prolonged period of time. As used in this specification and claims, the term "sustained release" is meant to refer to the latter situation.

Among the sustained release dosage forms is the 'depot dosage form', which comprise a pharmaceutically effective amount of TMC278 and a sustained release carrier, wherein TMC278 is released in such way that the blood plasma concentrations are kept at the values specified above. Depot dosage forms are meant to comprise those dosage forms in which amounts of the active ingredient is deposited into parts of the body from which it is slowly released during relatively long periods of time. The depot dosage injections may be used to further promote the slow release of the active ingredient from the site of deposition, keeping efficacious blood plasma levels of the HIV inhibitor for even longer periods such as several months.

For example, the active ingredient TMC278 may be encapsulated into small polymeric microspheres, which degrade slowly and release the active ingredient at a controlled rate. One form of microspheres are those wherein the active ingredient is encapsulated in a biodegradable polymer such as polylactide/polyglycolide polymers or copolymers. Another polymer based technology is the ReGel™ technology from MacroMed which uses triblock copolymers of poly(lactide-co-glycolide) and polyethylene glycol. These are thermosensitive and biodegradable polymers that become a gel upon heating and return to their original state upon cooling. These polymers/hydrogels systems are applied as solutions at administration temperature and become insoluble gels at the injection site. An insoluble gel depot is formed immediately upon injection and remains at the site for a period of several weeks. Drug release is controlled through a combination of diffusion from and degradation of the polymer. Another type of sustained release injectable dosage forms are based on liposomal systems which can be used in case of lipophilic drugs or lypophilically modified pro-drugs. The liposome particles can be coated, e.g. with polyethylene glycol to evade the immune system. Still another type of sustained release injectable dosage forms are the microscopic, spherical particles known as DepoFoam™ from SkyePharma. These particles, which are essentially lipid in nature, contain a multitude of small aqueous chambers encapsulating the drug to be delivered.

The parenteral dosage forms of TMC278, when administered in accordance with the present invention provide effective prevention of HIV infection. The limited number of drug administrations and the lack of undesirable side effects adds to the patients' compliance with the prescribed dosing. Patients' compliance may further be improved when selecting parenteral formulations showing good local tolerance, in particular showing minimal irritation and inflammation at the site of injection.

In one embodiment, the parenteral dosage forms of TMC278 are administered only once. This may be recommended in instances where individuals need protection against infection during a specific period of time, for example when traveling to countries with high prevalence of HIV infection or in case of medical personal treating only incidentally patients infected or potentially infected with HIV. In these instances, the parenteral formulation preferably is administered prior to the exposure or potential exposure to the risk of HIV infection, as a precautionary measure.

Thus, in a further aspect, there is provided the use of a parenteral formulation comprising an effective amount of TMC278 or a pharmaceutically acceptable acid-addition salt thereof, and a carrier, for the manufacture of a medicament for the long term prevention of HIV infection in an individual at risk of being infected by HIV, wherein the formulation is administered once. In another aspect the invention relates to a method for the long term prevention of HIV infection in an individual at risk of being infected by HIV, said method comprising administering to said individual an effective amount of TMC278 or a pharmaceutically acceptable acid-addition salt thereof, and a carrier, wherein the formulation is administered once.

The parenteral formulations of TMC278 for use in accordance with the present invention may be used in a similar manner as a vaccine. One or a series of injections at specific time intervals may provide protection against infection by HIV. An individual running a one time risk of being infected may be treated only once. Those running a permanent risk, such as those treating HIV-infected patients, may be treated by recurring injections at specific time intervals which for convenience can be selected to be relatively long time intervals such as 3 or 6 months or even longer.

Examples

The present study was performed in order to study the plasma kinetics and the absolute bioavailability of TMC278 in beagle dogs after single intramuscular administration (IM) of an aqueous 30% dimethylacetamide (DMA)/50% polyethylene glycol 400 (PEG400) solution of TMC278 at 2.5 mg/kg. The dogs were dosed IM.

Two male beagle dogs (dog No. 16924 and 16854), approximately 3 years old and weighing between 11 and 12 kg at the start of the experimental phase, were used in the present experiment. The dogs were dosed intramuscularly at 0.1 ml/kg body weight by injecting the formulation in the left (dog No. 16924) or right (dog No. 16854) m. biceps femoris.

One day before dose administration, TMC278 was formulated in an aqueous 30% (w/v) DMA/50% (w/v) PEG400 solution at 25 mg/ml. The ingredients of the solution were: TMC278, DMA 30% (w/v), PEG 400 50% (w/v) and pyrogenic free water. The content of TMC278 in the formulation was checked using LC. The concentration of TMC278 in the formulation was 25 mg/ml.

Blood samples (4 ml on EDTA) were taken from a jugular vein from the dogs at 0 (=predose), 0.5, 1, 2, 4, 8, 24, 32, 48, 72, 96, 144, 192, 240 and 312 h after dose administration. After sampling, the blood samples were immediately placed on melting ice and protected from light. Blood samples were centrifuged at approximately 1900×g for 10 minutes at 5° C. to allow plasma separation. Immediately after separation, plasma samples were protected from light, placed on melting ice and stored at ≤−18° C. until analysis. Frozen plasma samples were transferred to the Bioanalytical Department. Since TMC278 was still detectable in the plasma samples at 312 h post-dose, additional blood samples of both dogs were collected on the days 36, 50, 64, 78, 92, 106, 120, 134 and 148. These samples were analogously processed and analysed.

On day 232 post-dose, a biopsy was performed (dog No. 16924 only) on the iliac lymph node (at the side of injection), on a muscle from the non-injected hind leg and on a muscle at the side of injection after ultrasonographic examination. All tissue samples were protected from light as much as possible and stored on melting ice. All samples were protected from light and stored at ≤−18° C. Finally, an additional blood sample was collected on day 272. This sample was processed and analysed similarly to the other blood samples.

The concentration of TMC278 in dog plasma was determined by a qualified research LC-MS/MS method after solid phase extraction (SPE). Plasma concentrations of TMC278 were determined after proper sample clean up. The samples (0.1 ml aliquots of plasma) were extracted using a solid phase extraction method (Bond Elut Certify solid phase columns, 130 mg, SPE, Varian). The SPE column was conditioned with 3 ml methanol, 3 ml water and 1 ml acetic acid 1 M.

After addition of 3 ml acetic acid to 0.1 ml aliquots of plasma, the samples were extracted on the column followed by washing the column with 1 ml water, 1 ml acetic acid 1 M and 3 ml methanol. The column was eluted with 3 ml methanol/NH$_4$OH 25% (98:2, v/v). The extract was evaporated to dryness and reconstituted in 150 µl of ammonium formate 0.01 M (adjusted to pH 4 with formic acid)/methanol (50/50). 20 µl-aliquots were injected onto a reversed phase LC-column (100×4.6 mm ID, packed with 3 µm Hypersil C18 BDS) with a flow of 800 µl/min. The elution mixture was ammonium formate 0.01 M (adjusted to pH 4 with formic acid)/methanol (40:60, v/v). The flow-rate to the mass spectrometer was about 100 µl/min after splitting. LC-MS/MS analysis was carried out on an API-3000 system (Applied Biosystems), which was coupled to an HPLC-system.

The concentration of TMC278 in dog tissue samples was also determined by a qualified research LC-MS/MS method. Tissues samples were homogenized with a 10-fold dilution in Milli-Q water by means of an Ultra-Turrax. The tissue homogenates (200 µl aliquot) were extracted by adding of 600 µl methanol (containing TMC278 and/or methanol). After vortexing and centrifugation, the supernatant was transferred to an HPLC vial and 20 µl aliquots were injected. The LC and the MS conditions were the same as described above. The lower limit of quantification was 10.0 ng/g tissue. Samples were protected from light during the bioanalytical analysis.

Individual plasma concentration-time profiles were subjected to a non-compartmental pharmacokinetic analysis. Peak plasma concentrations ($C_{max}$) and corresponding peak times ($T_{max}$) were determined. The AUC from time 0 to time t ($AUC_{0-t}$, where t is the time point associated with the last measurable concentration above the limit of quantification) was calculated by means of the linear/log trapezoidal rule: i.e. linear trapezoidal rule up to $T_{max}$: $AUC_{0-Tmax}=\Sigma[(t_{i+1}-t_i) \cdot (C_i+C_{i+1})/2]$, and log trapezoidal for the remainder of the curve: $AUC_{Tmax-t}=\Sigma[(t_{i+1}-t_i) \cdot (C_i-C_{i+1})/\ln(C_i/C_{i+1})]$, $C_i$ and $C_{i+1}$ being the plasma concentrations at times $t_i$ and $t_{i+1}$, respectively. The area under the curve extrapolated to infinity ($AUC_{0-\infty}$) and the absolute bioavailability of TMC278 in the present formulation could not be calculated adequately since plasma concentrations remained fairly constant or slightly increased between 72 h and 312 h after dosing. The half-life was calculated between 1 h and 24 h ($t_{1/2,\ 1-24\ h}$) or 8 h and 24 h ($t_{1/2,\ 8-24\ h}$) and between 24 h and 72 h post-dose ($t_{1/2,\ 24-72}$ h) according to $t_{1/2}=\ln(2)/k$, with k corresponding to the rate constant over the respective time ranges. Mean (n=2) plasma concentrations and pharmacokinetic parameters were calculated.

Individual and mean (n=2) plasma concentrations and/or some basic pharmacokinetic parameters are reported in Table 1 and Table 2. Tissue levels (iliac lymph node, muscle), collected on day 232 after dosing, are showed in the Table 3.

After intramuscular administration of an aqueous 30% DMA/50% PEG400 solution of TMC278 at 2.5 mg/kg, mean peak plasma concentrations ($C_{max}$) amounted to 31.9 ng/ml. The individual peak plasma levels were reached within 1 to 8 h after dosing. After $C_{max}$, plasma levels declined rapidly till 24 h post-dose, followed by a more slowly decline up to 72 h after dosing with an half-life ($t_{1/2,\ 24-72\ h}$) of 63 h. After 72 h post-dose, plasma levels remained fairly constant or slightly increased up to 312 h post-dose. The mean $AUC_{0-312\ h}$ value amounted to 1863 ng·h/ml.

Since plasma concentrations remained fairly constant or slightly increased between 72 h and 312 h post-dose, additional blood samples were taken on the days 36, 50, 64, 78, 92, 106, 120, 134 and 148. During this wash-out period, plasma levels remained fairly constant (range: 1.24-4.23 ng/ml). Therefore, a biopsy was performed on the iliac lymph node (at the side of injection), on a muscle from the non-injected hind leg and on a muscle at the side of injection. The biopsy was performed on day 232 in dog No. 16924 only. The levels of TMC278 in the muscles were below the limit of quantification (10.0 ng/g). The level in the lymph node amounted to 72.6 ng/g, which was high with respect to the plasma concentrations on day 148 (i.e. on average 1.33 ng/ml) and on day 272 (<1.00 ng/ml).

TABLE 1

Individual and mean (n = 2) plasma concentrations (ng/ml) and some basic pharmacokinetic parameters of TMC278 in beagle dogs after single intramuscular administration of an aqueous 30% DMA/50% PEG400 solution of TMC278 at 2.5 mg/kg.

| | | Dosage group 2.5 mg/kg Dog No. | | |
|---|---|---|---|---|
| Time (h) | | 16854 | 16924 | Mean |
| 0 | | <1.00 | <1.00 | <1.00 |
| 0.5 | | 13.5 | 21.3 | 17.4 |
| 1 | | 17.0 | 23.8 | 20.4 |
| 2 | | 20.6 | 20.9 | 20.8 |
| 4 | | 27.2 | 17.1 | 22.2 |
| 8 | | 39.9 | 15.1 | 27.5 |
| 24 | | 11.4 | 7.70 | 9.55 |
| 32 | | 10.7 | 6.65 | 8.68 |
| 48 | | 9.03 | 6.03 | 7.53 |
| 72 | | 7.37 | 3.90 | 5.64 |
| 96 | | 6.40 | 3.97 | 5.19 |
| 144 | | 3.19 | 3.65 | 3.42 |
| 192 | | 2.80 | 3.57 | 3.19 |
| 240 | | 6.16 | 4.38 | 5.27 |
| 312 | | 4.24 | 5.97 | 5.11 |
| $C_{max}$ | ng/ml | 39.9 | 23.8 | 31.9 |
| $T_{max}$ | h | 8 | 1 | 5 |
| $t_{1/2,\ 1-24\ h}$ | h | 8.9[1] | 15.1 | NC[2] |
| $t_{1/2,\ 24-72\ h}$ | h | 75.2 | 51.0 | 63.1 |
| $AUC_{0-312\ h}$ | ng·h/ml | 2122 | 1603 | 1863 |

[1] $t_{1/2,\ 8-24\ h}$
[2] NC: Not calculated.

TABLE 2

Individual and mean (n =2) plasma concentrations (ng/ml) of TMC278 in beagle dogs during the wash-out period after single intramuscular administration of an aqueous 30% DMA/50% PEG400 solution of TMC278 at 2.5 mg/kg.

| | Dosage group 2.5 mg/kg Dog No. | | |
|---|---|---|---|
| Day | 16854 | 16924 | Mean |
| 36 | 3.66 | 3.05 | 3.36 |
| 50 | 4.10 | 2.12 | 3.11 |
| 64 | 2.18 | 2.42 | 2.30 |
| 78 | 2.62 | 1.69 | 2.16 |
| 92 | 2.32 | 2.51 | 2.42 |
| 106 | 2.02 | 1.75 | 1.89 |
| 120 | 1.87 | 4.23 | 3.05 |
| 134 | 1.67 | 1.61 | 1.64 |

TABLE 2-continued

Individual and mean (n =2) plasma concentrations (ng/ml) of TMC278 in beagle dogs during the wash-out period after single intramuscular administration of an aqueous 30% DMA/50% PEG400 solution of TMC278 at 2.5 mg/kg.

| | Dosage group 2.5 mg/kg Dog No. | | |
|---|---|---|---|
| Day | 16854 | 16924 | Mean |
| 148 | 1.41 | 1.24 | 1.33 |
| 272 | ND[1] | <1.00 | ND |

[1] ND: Not determined.

TABLE 3

Tissue concentrations (ng/g) of TMC278 in beagle dogs on day 232 after single intramuscular administration of an aqueous 30% DMA/50% PEG400 solution of TMC278 at 2.5 mg/kg.

| Tissue | Dosage group 2.5 mg/kg Dog No. 16924 |
|---|---|
| iliac lymph node at the side of injection | 72.6 |
| muscle from the non-injected hind leg | <10.0 |
| muscle at the side of injection | <10.0 |

The invention claimed is:

1. A method of maintaining a blood plasma level of 4-1000 ng/ml of 4-[[4-[[4-(2-cyanoethenyl)-2,6-dimethylphenyl]amino]-2-pyrimidinyl]-amino]benzonitrile, the E isomeric form thereof or the Z-isomeric form thereof in an individual at risk of being infected with HIV-1, comprising
   subcutaneously or intramuscularly injecting a solution into the individual, intermittently at a time interval of at least one week, wherein said solution comprises:
   sterile water;
   a solubilizer or a surfactant; and
   a dose, calculated on a basis of 0.2 mg/day to 50 mg/day of the time interval, of 4-[[4-[[4-(2-cyanoethenyl)-2,6-dimethylphenyl]amino]-2-pyrimidinyl]-amino]benzonitrile, the E isomeric form thereof or the Z-isomeric form thereof; or a pharmaceutically acceptable acid-addition salt thereof;
   wherein the blood plasma level is maintained over the time interval.

2. The method according to claim 1 wherein the administration time interval is once every 3, 4, 6, 7, or 8 weeks.

3. The method according to claim 1 wherein the administration time interval is once every 1, 2, or 3 months.

4. The method according to claim 1 wherein the administration time interval is once every month.

5. The method according to claim 1 wherein the administration time interval is once every three months.

6. The method according to claim 1 wherein the blood plasma level of 4-[[4-[[4-(2-cyanoethenyl)-2,6-dimethylphenyl]amino]-2-pyrimidinyl]-amino]benzonitrile, the E isomeric form thereof or the Z-isomeric form thereof is maintained over the time interval at a level equal to or above 15 ng/ml.

7. The method according to claim 1 wherein the blood plasma level of 4-[[4-[[4-(2-cyanoethenyl)-2,6-dimethylphenyl]amino]-2-pyrimidinyl]-amino]benzonitrile, the E isomeric form thereof or the Z-isomeric form thereof is maintained over the time interval at a level equal to or above 20 ng/ml.

8. The method according to claim 1 wherein the blood plasma level of 4-[[4-[[4-(2-cyanoethenyl)-2,6-dimethylphenyl]amino]-2-pyrimidinyl]-amino]benzonitrile, the E isomeric form thereof or the Z-isomeric form thereof is maintained over the time interval at a level equal to or above 40 ng/ml.

9. The method according to claim 1 wherein the blood plasma level of 4-[[4-[[4-(2-cyanoethenyl)-2,6-dimethylphenyl]amino]-2-pyrimidinyl]-amino]benzonitrile, the E isomeric form thereof or the Z-isomeric form thereof is maintained over the time interval at a level below 40 ng/ml and above 4 ng/ml.

10. The method according to claim 1 wherein the solubilizer is a cyclodextrin or a cyclodextrin derivative or a polyethylene glycol.

11. The method according to claim 1, wherein the 4-[[4-[[4-(2-cyanoethenyl)-2,6-dimethylphenyl]amino]-2-pyrimidinyl]-amino]benzonitrile, the E isomeric form thereof or the Z-isomeric form thereof; or a pharmaceutically acceptable acid-addition salt thereof is in base-form.

12. The method according to claim 1 wherein the 4-[[4-[[4-(2-cyanoethenyl)-2,6-dimethylphenyl]amino]-2-pyrimidinyl]-amino]benzonitrile occurs in its E-isomeric form.

13. The method according to claim 11 wherein the base form of the 4-[[4-[[4-(2-cyanoethenyl)-2,6-dimethylphenyl]amino]-2-pyrimidinyl]-amino]benzonitrile, occurs in its E-isomeric form.

14. The method according to claim 1 wherein the administration time interval is once every two months.

15. The method according to claim 3 wherein the time interval is 30 days and the dose of the 4-[[4-[[4-(2-cyanoethenyl)-2,6-dimethylphenyl]amino]-2-pyrimidinyl]-amino]benzonitrile, the E isomeric form thereof or the Z-isomeric form thereof, ranges from 15 mg to 1,500 mg.

16. The method according to claim 3 wherein the time interval is 28 days and the dose of the 4-[[4-[[4-(2-cyanoethenyl)-2,6-dimethylphenyl]amino]-2-pyrimidinyl]-amino]benzonitrile, the E isomeric form thereof or the Z-isomeric form thereof, ranges from 14 mg to 1,400 mg.

17. The method according to claim 1 wherein the dose is calculated on a basis of 1 mg/day to 10 mg/day.

18. The method according to claim 3, wherein the time interval is 29 days and the dose of the 4-[[4-[[4-(2-cyanoethenyl)-2,6-dimethylphenyl]amino]-2-pyrimidinyl]-amino]benzonitrile, the E isomeric form thereof or the Z-isomeric form thereof, ranges from 14.5 mg to 1,450 mg.

19. The method according to claim 3, wherein the time interval is 31 days and the dose of the 4-[[4-[[4-(2-cyanoethenyl)-2,6-dimethylphenyl]amino]-2-pyrimidinyl]-amino]benzonitrile, the E isomeric form thereof or the Z-isomeric form thereof, ranges from 15.5 mg to 1,550 mg.

20. The method according to claim 3, wherein the time interval is about one month and the dose of the 4-[[4-[[4-(2-cyanoethenyl)-2,6-dimethylphenyl]amino]-2-pyrimidinyl]-amino]benzonitrile, the E isomeric form thereof or the Z-isomeric form thereof, ranges from about 15 mg to about 1,500 mg.

21. The method according to claim 3, wherein the dose is about 30 mg to about 300 mg.

22. The method according to claim 3, wherein the dose is about 60 mg to about 150 mg.

23. The method according to claim 1 wherein the administration time interval is once every 4 weeks.

24. The method according to claim 1 wherein the administration time interval is once every 8 weeks.

* * * * *

UNITED STATES PATENT AND TRADEMARK OFFICE
CERTIFICATE OF CORRECTION

Page 1 of 1

PATENT NO.        : 10,765,674 B2
APPLICATION NO.   : 15/180391
DATED             : September 8, 2020
INVENTOR(S)       : Baert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 502 days.

Signed and Sealed this
Eighth Day of June, 2021

Drew Hirshfeld
*Performing the Functions and Duties of the
Under Secretary of Commerce for Intellectual Property and
Director of the United States Patent and Trademark Office*